United States Patent [19]

Jagger et al.

[11] Patent Number: 4,592,744

[45] Date of Patent: Jun. 3, 1986

[54] SELF-RESHEATHING NEEDLE ASSEMBLY

[75] Inventors: Janine C. Jagger; Richard D. Pearson; Patrice G. Guyenet, all of Charlottesville; Jessica J. Brand, Earlysville, all of Va.

[73] Assignee: The University of Virginia Alumni Patents Foundation, Charlottesville, Va.

[21] Appl. No.: 765,397

[22] Filed: Aug. 14, 1985

[51] Int. Cl.[4] .............................................. A61M 5/32
[52] U.S. Cl. ................................... 604/192; 604/197; 128/763
[58] Field of Search ............... 604/196, 197, 192, 193, 604/198, 194, 195, 110, 263; 128/763, 765

[56] References Cited

U.S. PATENT DOCUMENTS

| 2,888,923 | 6/1959 | Reis | 604/195 |
| 2,925,083 | 2/1960 | Craig | 604/197 |
| 3,356,089 | 12/1967 | Francis | 604/197 X |
| 4,507,117 | 3/1985 | Vining et al. | 604/196 |

Primary Examiner—John D. Yasko
Attorney, Agent, or Firm—James C. Wray

[57] ABSTRACT

A self-resheathing safety needle has a case with a small closed end and a large open end and a needle assembly within the case with the needle projecting through the small closed end. A hub is connected to the needle assembly inside the case and a connector on the hub cooperates with a receiver in the small end to hold the needle assembly in the case. A flange on the hub cooperates with an inward projection in the case spaced from the small end to prevent movement of the needle out of the case when the needle is withdrawn from the opening in the small end. The nozzle of a syringe pushed into the hub withdraws the needle when the syringe is withdrawn. A rubber stopper on a vacuum tube withdraws the needle after the rubber stopper turns the flange to release the connector from the receiver.

30 Claims, 6 Drawing Figures

SELF-RESHEATHING NEEDLE ASSEMBLY

BACKGROUND OF THE INVENTION

Accidental needle stick injuries are extremely common in health care workers, such as nurses, physicians, laboratory workers, and housekeeping personnel. Needle stick exposures can result in transmission of hepatitis B, non A non B hepatitis, and potentially, the acquired immunodeficiency syndrome—AIDS, or other transmissable diseases. The health hazards associated with needle stick injuries are of greater risk for health care workers in the 1980's than ever before. Furthermore, each reported needle stick injury costs a hospital more than $200.

Accidental needle sticks often occur when a blood drawer attempts to recap a needle after use or leaves a contaminated needle exposed on work surfaces where the blood drawer or other workers accidentally impale themselves.

A modification of the current vacuum tube phlebotomy system is urgently needed to provide a protective barrier between health care workers and exposed, contaminated needles.

The following is a list of patents which exemplify the state of the art. U.S. Pat. Nos. 4,392,859, 4,373,526, 4,273,123, 4,266,544, 4,139,009, 3,890,971, 3,485,239, 3,306,291, 3,306,290, 2,847,996, 2,847,995.

U.S. Pat. No. 4,392,859 teaches an automatic injecting device having a spring biased retracting needle.

U.S. Pat. No. 4,373,526 teaches a needle maintained within a barrel.

U.S. Pat. No. 4,273,123 teaches a protective closure for a needle of a hypodermic which may receive and retain the needle after it is removed from or broken off the end of the syringe. It is believed someone must recap the needle before they break it off the end of the syringe so this invention does not obviate the problem of injuring oneself upon recapping a needle.

U.S. Pat. No. 4,266,544 teaches a device on the end of a syringe apparatus which renders a needle inoperable subsequent to being used.

U.S. Pat. No. 4,139,009 teaches a retractable cover means for a hypodermic.

U.S. Pat. No. 3,890,971 teaches a safety feature for syringes which, subsequent to being used, locks the plunger and needle such that it is incapable of being reused.

U.S. Pat. No. 3,485,239 teaches a self contained syringe where the hypodermic is initially situated within a barrel.

U.S. Pat. No. 3,306,291 teaches the use of frangible connections in combination with syringes and the like.

U.S. Pat. No. 3,306,290 teaches the use of a spring biased retractable syringe.

U.S. Pat. No. 2,847,996 teaches the use of a hypodermic having two barrel-like compartments.

U.S. Pat. No. 2,847,995 shows the use of a retractable needle within a rubber sheath.

A need persists for apparatus to avoid needle stick accidents.

SUMMARY OF THE INVENTION

Briefly, the present invention concerns safety venipuncture devices having needle retracting means, particularly hypodermic needles having a retractable needle, vacuum tube phlebotomy systems having retractable needles, and intravenous devices having retractable needles. Each one of the different devices, hypodermics, vacuum tube phlebotomy systems, and intravenous administration sets, has a similar feature. The feature is designed to solve the problem of recapping or disposing of the needle portion of the apparatus subsequent to use. The invention solves the problem of disposing of contaminated needles by retracting the needle within a barrel, whereupon the barrel is disposed of, obviating any possibility of a contaminated needle injuring anyone.

In one embodiment of the invention a resheathing syringe-needle system allows entrapment of the contaminated needles in plastic compartments to prevent injury and the spread of hepatitis B, AIDS or other diseases to health care personnel. A standard syringe and needle are mounted in a clear plastic sheath. The needle extends through a hole in the bottom of the sheath. The end of the needle is covered with a cap. To use, the cap is removed and the standard medical procedures are carried out in the usual way but with the syringe still inside of the clear plastic sheath. After use, the syringe and needle are drawn back into the sheath until the needle is completely within the confines of the plastic sheath. Flanges within the sheath catch behind the lip of the needle as the syringe is withdrawn, trapping the needle inside of the sheath. The needle is thus unable to protrude at either end. The syringe can either be removed or the entire syringe-needle-sheath assembly can be disposed of as a unit without risk of accidental needle stick injury to medical and hospital personnel.

Under some circumstances it may be necessary to use two needles in succession for a single medical procedure. Such is the case when drawing blood for blood cultures. Currently, the blood is drawn with the first needle. To transfer the blood to a sterile container the contaminated needle is replaced with a sterile needle. Thus, one procedure produces two contaminated needles. Our system provides a solution for this situation by packing individual needles in empty clear plastic sheaths. A blood-filled syringe can be withdrawn from the first sheath, leaving the first needle trapped for disposal. The syringe is then inserted into a needle-mounted sheath without a syringe and couples with the new needle. After emptying the blood-filled syringe into the sterile container, the syringe is pulled back, trapping the second needle in its protective sheath.

In another embodiment of the invention a self-resheathing safety needle of the present invention is used for vacuum tube phlebotomy. The system may be used, as is common medical practice, to draw as many tubes of blood as desired. The unit consists of three basic parts: (1) the vacuum tubes remain unaltered in the present design, (2) the clear plastic sheath into which the vacuum tubes are inserted to connect with the needle assembly and (3) the needle assembly which includes both the internal and external needles.

The needle assembly differs from current designs in that the assembly is screwed into the inside of the sheath. The needle can therefore be removed only by unscrewing it towards the inside of the sheath. The external needle protrudes from the sheath through a small gauge hole. A further innovation in the design of the needle assembly is the addition of a broad collar at the junction of the internal and external needles. This collar is slightly larger than the diameter of the rubber stopper of a vacuum tube and has a number of directional teeth projecting from the surface making contact with the rubber stopper.

The clear plastic sheath differs from current designs in that the screw threads for connecting the needle assembly are located on the inside of the sheath, as mentioned above. There is a constriction in the diameter of the sheath at a distance from the needle hole slightly greater than the length of the external needle. The opening in this constriction must be larger than the widest part of the vacuum tube and smaller than the diameter of the needle collar. The total length of the sheath must be longer than the needle assembly.

The system is used in the conventional way by inserting the external needle into a blood vessel. The blood is drawn into a vacuum tube that has been inserted into the sheath and pushed onto the internal needle. Several tubes of blood may be drawn in succession by simply withdrawing one tube and inserting another. When the last tube of blood has been drawn, the system is withdrawn from the patient's vein as a unit. Then forward pressure is applied to the vacuum tube which causes the rubber stopper to make contact with the needle collar engaging the teeth. The tube is then rotated within the sheath causing the needle assembly to unscrew towards the inside of the sheath. When the needle assembly has disengaged, the tube is withdrawn, pulling the needle assembly with it. Friction between the inner needle, which is still in place, and the rubber top of the vacuum tube makes this possible. The needle assembly is then captured within the confines of the sheath as the tube disengages because the collar cannot advance beyond the constriction. The small gauge hole prevents the external needle from sliding back out. The internal needle is shielded by the sheath which extends slightly beyond its length.

This system requires that the sheath be disposable. It entirely avoids the hazardous maneuvers of recapping and unscrewing the used needle assembly. Furthermore, both ends of the needle are shielded by a hard plastic barrier for safer disposal, whereas before only one end was capped with rigid plastic. With this system, it would be difficult for hospital personnel to accidentally stick themselves with a contaminated needle assembly. This is because the needle assembly never needs to be touched once it is used, and the spent needle assembly is permanently trapped in a rigid plastic casing. This sytem will prevent injury and the spread of hepatitis B, AIDS or other diseases by needle stick injury.

A preferred disposable medical needle apparatus comprises a case having an elongated cavity surrounded by a longitudinally extending wall. The cavity has a first relatively open end at a first longitudinal end of the wall and has a second relatively closed end at a second opposite longitudinal end of the wall. The case has a needle-passing restricted opening in the second end, and the case has an inward extension near the first end for preventing passage of a needle assembly past the inward extension and holding a needle assembly within the cavity, whereby a needle assembly, after use, may be withdrawn from the opening and may be held within the cavity.

The preferred apparatus further comprises a receiver positioned in the second end of the case for receiving a needle assembly and releasably holding the needle assembly in the second end with a portion of a needle extending through the restricted opening in the second end.

The preferred apparatus further comprises a needle assembly having an elongated tubular needle with a sharp distal end and a hub surrounding a portion of the tubular needle for holding the tubular needle. The hub has a connector for releasably attaching the hub in the receiver, and the hub has an outward extending collar or flange for cooperating with the inward extension in the case to prevent passage of the needle assembly past the inward extension.

The preferred receiver comprises a generally cylindrical recess in the second end between the restricted opening and the cavity, and the connector comprises means for cooperating with the generally cylindrical wall.

In one preferred embodiment the connector comprises an externally longitudinally ribbed structure, whereby ribs releasably engage the generally cylindrical wall of the receiver.

In another preferred embodiment the cylindrical wall is threaded with female threads, and the connector is threaded with complementary male threads. Preferably, the threads are discontinuous for rapid disassembly upon relative partial turning.

One preferred flange has turning means for turning the flange and the needle assembly.

The preferred turning means are generally axially extending cleats of a face of the flange remote from a distal end of the needle.

In one preferred embodiment the needle projects inward in the cavity beyond the hub for puncturing a stopper on a vial inserted within the cavity.

Preferably the elastomeric turner comprises a stopper on a vial inserted in the cavity.

In one embodiment the longitudinally extending wall comprises a first portion having relatively large diameter extending from the second end to the inward extension and a second portion having a relatively small diameter extending from the inward extension to the first end.

In a preferred embodiment the second end of the case has a generally cylindrical outer wall for holding a snap-off cap covering a needle.

In a preferred embodiment the hub has a tapered recess for receiving a nozzle portion of a syringe body, and the inward extension is configured for permitting passage of the syringe body into the casing.

The preferred embodiment further comprises a syringe body having a nozzle portion tightly slidingly connected to the hub. The syringe body is mounted inside the cavity within the inward extension, and a plunger compressed in the syringe body. Preferably, the flange extends radially outward beyond the syringe body.

This invention provides a self-resheathing safety needle for vacuum tube phlebotomy.

The invention also provides a self-resheathing safety needle for syringes.

These and further objects and features of the invention are apparent in the disclosure which includes the above and ongoing specification with the claims and the drawings.

DETAILED DESCRIPTION OF THE DRAWINGS

Figures 1, 2, 3:
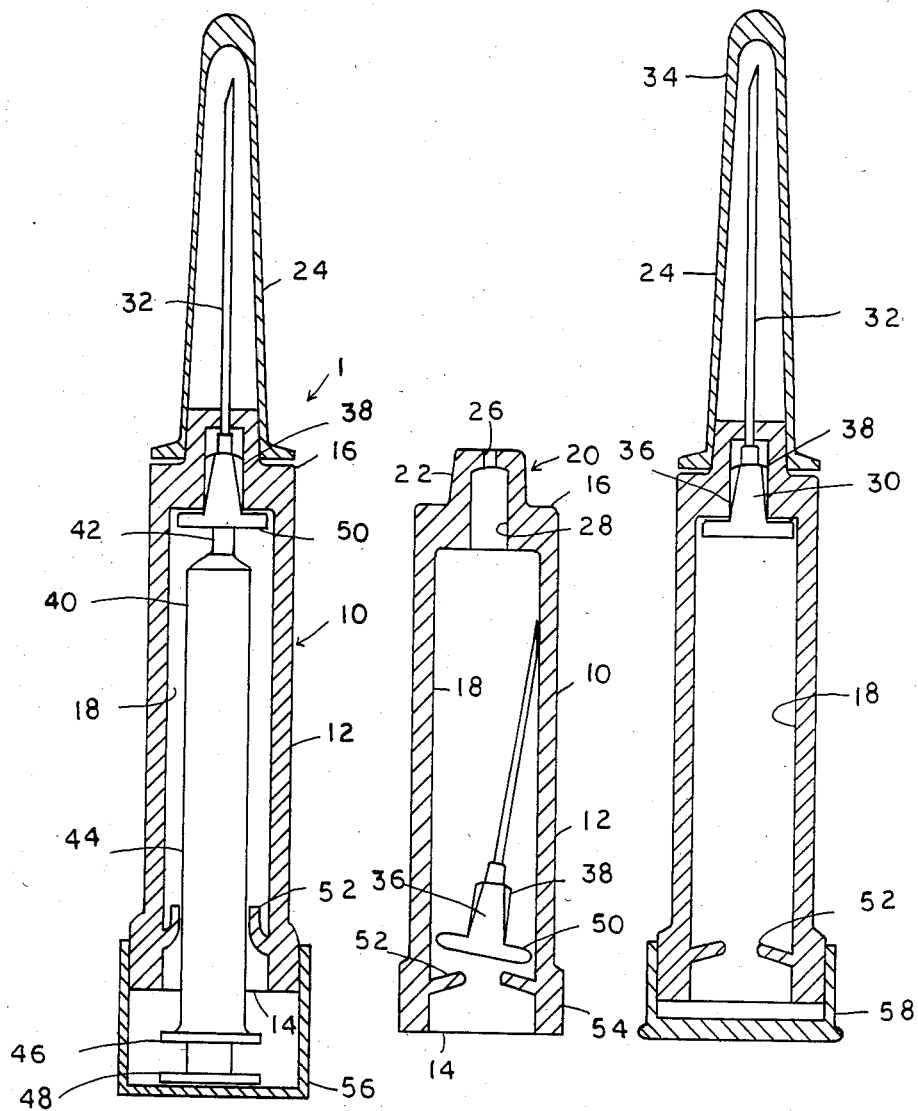
FIG. 1 shows a self-resheathing needle assembly and syringe of the present invention.
FIG. 2 shows the needle assembly after the needle is resheathed.
FIG. 3 shows one form of the invention in which the resheathing needle assembly is ready to receive a syringe once the large cap has been removed.

Referring to FIGS. 1–3, a self-resheathing needle assembly apparatus is generally indicated by the numeral 1. An elongated case 10 has a longitudinally extending wall 12. A first relatively large open end 14 is at one end of the case 10. The second end 16 is relatively closed. The inside of the wall 12 forms a cavity 18.

A nipple 20 on the closed end 16 has a generally cylindrical outer surface 22 for receiving the end of a rigid cover 24 which protects a needle extending through the small opening 16 and at closed end 16. The inside of the nipple 20 has a generally cylindrical wall forming a receiver 28.

A needle assembly 30 has an elongated needle 32 which projects through opening 26. Needle 32 has a sharpened distal end 34 and a proximal end which is tightly held by hub 36. The hub 36 has an outer wall with ridges 38 which act as a connector for holding the hub 36 and the needle assembly 30 in the receiver 28. Hub 36 contains a slightly tapered recess 39 which tightly engages a nozzle 42 of a syringe 40 inserted within the case 10. The syringe body 44 which fits within the cavity 18 has a distal end 46 which receives a plunger 48.

A collar or flange 50 on the hub 36 of the needle assembly 30 extends radially outward beyond the syringe body 44 in the preferred embodiment. Inward projections 52 which extend from wall 12 into the cavity 18 permit passage of the syringe body 44 but prevent outward passage of the flange 50.

After the syringe 40 has been used, the outward end 46 is grasped and pulled outward from case 10. The connector 38 is gripped within receiver 28 to a lesser extent than the gripping of the nozzle 42 within the recess 39 in hub 36. Thus, withdrawing the syringe 40 from the case 10 tends to pull the needle assembly 30 along with the syringe. When the flange 50 encounters the inward projections 52, the needle assembly 30 is prevented from further movement. The syringe 40 may be left attached to the needle assembly 30 and the entire device may be discarded together. Alternatively, further pulling on the syringe 40 withdraws the nozzle 42 from the recess 39 and separates the syringe from the needle assembly 30 so that the two devices may be separately discarded.

The entire needle 32 and its sharpened end 34 are automatically withdrawn into the casing 10 when the syringe 40 is withdrawn, so that there can be no danger of needle stick injury.

The preferred case 10 is manufactured with an enlarged end 54 which strengthens the inward extension 52 and which holds a cap 56 covering the extended end 46 and plunger 48 of the syringe 40.

In an alternate embodiment as shown in FIG. 3, a shorter cap 58 is removed before a syringe 40 is inserted into the case 10 and needle assembly 30.

Figure 4:
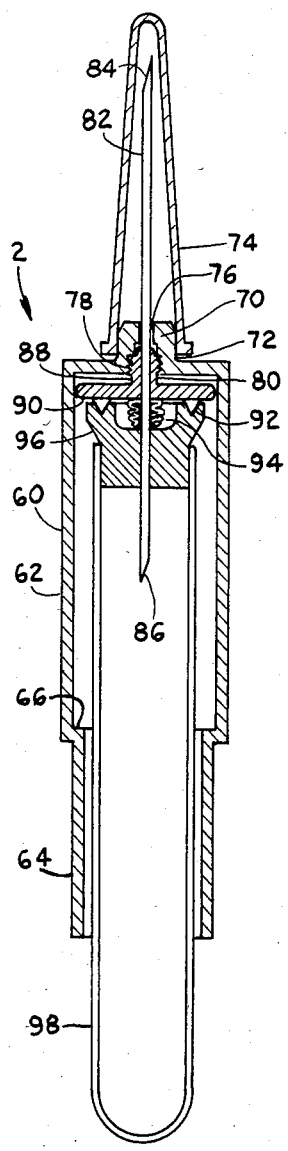
FIG. 4 represents a second embodiment of the invention used for phlebotomy.
Figure 5:
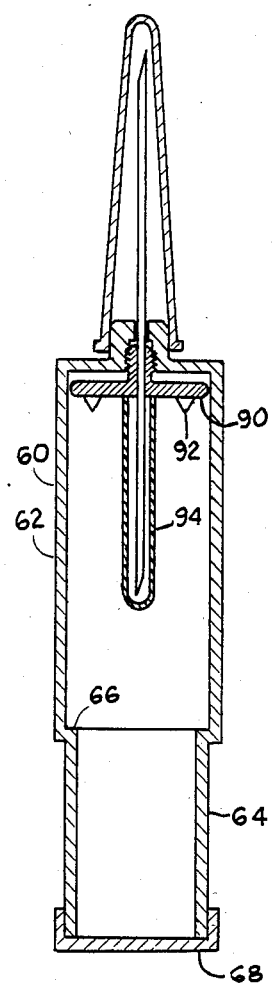
FIG. 5 shows the needle assembly used in the FIG. 4 embodiment in a condition ready for use once the protective cover has been removed from the needle.
Figure 6:
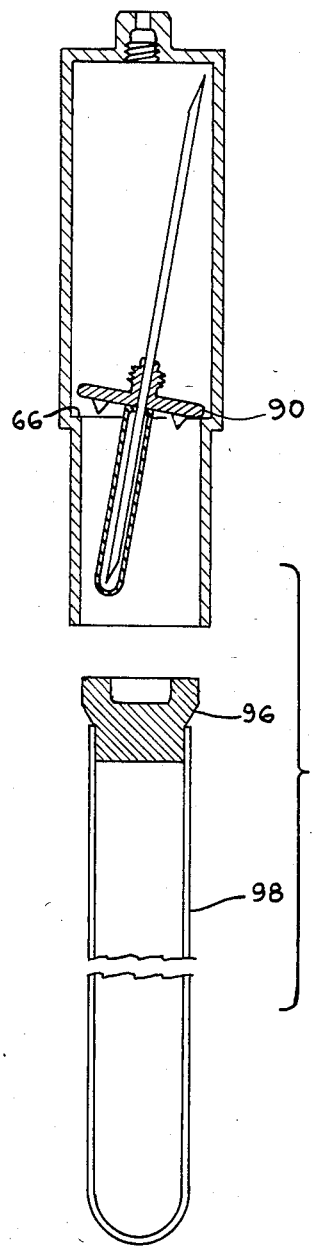
FIG. 6 shows the self-resheathing of the needle after the filled vacuum tube has been removed.

Referring to FIGS. 4, 5 and 6, the second embodiment of the invention is generally indicated by the numeral 2. A case 60 is made of a cylindrical wall having a first relatively large portion 62 near a closed end of the case, and a second relatively small portion 64 near an open end of the case 60. The large and small wall portions 62 and 64 are separated by an inward extension 66. The cap 68, as shown in FIG. 5, completes the case.

The closed end 70 is formed as a nipple with a cylindrical outer surface 72 for holding a rigid needle protecting cover 74. An opening 76 in a nipple 70 closely surrounds a needle which is held in receiver 78.

A needle hub 80 holds an elongated needle 82 having sharpened opposite distal and proximal ends, 84 and 86 respectively. Connector 88 on hub 80 is in the form of integral threads which cooperate with complementary threads on receiver 78 to hold the hub within the receiver. An integrally formed flange 90 on the hub has projections 92 which cooperate with a rubber stopper to turn the flange 90 and the hub 80 so that the threads on connector 88 are withdrawn from threads on receiver 78. A soft rubber sheath 94 covers the sharpened proximal end 86 of the needle before it is inserted through the rubber stopper 96 of the vial 98.

In use, the devices shift in the configuration shown in FIG. 5.

Cover 74 is removed, and the needle is inserted in a blood vessel, using case 60 as a handle. Then cap 68 is removed and a vacuum vial 98 is inserted in the case 60. Rubber stopper 96 is pierced by the sharpened proximal end 86 of needle 82, also forcing the sharpened needle through the protective sheath 94. The vial continues inward, compressing the protective sheath 94. As soon as the hollow needle completely pierces the stopper, the reduced pressure in vial 98 draws fluid through the needle into the vial. The vial of blood may be withdrawn from the casing and a new vial inserted in the casing, again piercing stopper 96 with the needle point 86. After sufficient blood has been withdrawn, the needle is pulled from the vessel by pulling on casing 60 and the vial is turned, turning cleats 92 and flange 90 and the threaded connector 88 on hub 80 until the threads on the connector are free of threads in receiver 78. Pulling outward on vial 98 draws the needle 82 and its hub 80 rearward until flange 90 contacts the inward extension 66. Further pulling outward on the vial pulls the needle from the rubber stopper, leaving the case 60 with the needle entrapped ready to be discarded.

While the invention has been described with reference to specific embodiments, modifications and variations may be constructed without departing from the scope of the invention. The scope of the invention is defined in the following claims.

We claim:

1. A disposable medical needle apparatus comprising a case having an elongated cavity surrounded by a longitudinally extending wall, the cavity having a first relatively open end at a first longitudinal end of the wall and having a second relatively closed end at a second opposite longitudinal end of the wall, the case having a needle-passing restricted opening in the second end, and the case having an inward extension near the first end for preventing passage of a needle assembly past the inward extension and holding a needle assembly within the cavity, wherby a needle assembly, after use, may be withdrawn from the opening and may be held within the cavity.

2. The apparatus of claim 1 further comprising a receiver positioned in the second end of the case for receiving a needle assembly and releasably holding the needle assembly in the second end with a portion of a needle extending through the restricted opening in the second end.

3. The apparatus of claim 1 further comprising a needle assembly having an elongated tubular needle with a sharp distal end, a hub surrounding a portion of the tubular needle for holding the tubular needle, the hub having a connector for releasably attaching the hub in the receiver and the hub having an outward extending flange for cooperating with the inward extension in the case to prevent passage of the needle assembly past the inward extension.

4. The apparatus of claim 3 wherein the receiver comprises a generally cylindrical recess in the second end between the restricted opening and the cavity, and wherein the connector comprises means for cooperating with the generally cylindrical wall.

5. The apparatus of claim 4 wherein the connector comprises an externally longitudinally ribbed structure, whereby ribs releasably engage the generally cylindrical wall of the receiver.

6. The apparatus of claim 4 wherein the cylindrical wall is threaded with female threads and wherein the connector is threaded with complementary male threads.

7. The apparatus of claim 6 wherein the threads are discontinuous for rapid disassembly upon relative partial turning.

8. The apparatus of claim 6 wherein the flange has turning means for turning the flange and the needle assembly.

9. The apparatus of claim 8 wherein the turning means are generally axially extending cleats of a face of the flange remote from a distal end of the needle.

10. The apparatus of claim 9 wherein the cleats are sloped in one sense of rotation to provide unidirectional disengaging rotation by the cleats contacting an elastomeric turner.

11. The apparatus of claim 6 wherein the needle hub has a proximal end within the hub.

12. The apparatus of claim 11 wherein the needle projects inward in the cavity beyond the hub for puncturing a stopper on a vial inserted within the cavity.

13. The apparatus of claim 10 wherein the elstomeric turner comprises a stopper on a vial inserted in the cavity.

14. The apparatus of claim 13 further comprising a generally radially inward extension on the longitudinally extending wall.

15. The apparatus of claim 14 wherein the longitudinally extending wall comprises a first portion having relatively large diameter extending from the second end to the inward extension and a second portion having a relatively small diameter extending from the inward extension to the first end.

16. The apparatus of claim 4 wherein the second end has a generally cylindrical outer wall for holding a snap-off cap covering a needle.

17. The apparatus of claim 3 wherein the hub comprises a tapered recess for receiving a nozzle portion of a syringe body and wherein the inward extension is configured for permitting passage of the syringe body into the casing.

18. The apparatus of claim 17 further comprising a syringe body having a nozzle portion tightly slidingly connected to the hub, the syringe body being mounted inside the cavity within the inward extension and a plunger compressed in the syringe body, and wherein the flange extends radially outward beyond the syringe body.

19. A self-resheathing safety needle for vacuum tube phlebotomy comprising a longitudinally extending case having a first relatively open end and a second relatively closed end and having a wall extending between the first and second ends thereby forming a cavity, an inward extension on the wall extending inward in the cavity near the first end for preventing passage of a needle assembly, the second end having a central nipple portion extending outward from the case for receiving a snap-off needlecovering cap, and the second end having a receiver for receiving and releasably holding a needle assembly, a needle assembly having an elongated needle sharpened at opposite distal and proximal ends and a hub mounted medially on the needle and tightly gripping the needle intermediate the opposite ends, the hub having a connector for cooperating with the receiver to releasably hold the hub in the receiver with a distal end portion of the needle extending through a small opening in the nipple, the hub further having a flange for contacting the inward extension when the needle is released from the receiver and is withdrawn into the cavity and thereby and preventing outward egress of the needle assembly from the cavity through the first end of the case.

20. The apparatus of claim 19 wherein the flange has cleats projecting toward the first end for contacting a stopper of a vacuum tube when a vacuum tube stopper is pushed on the sharpened end of the needle which projects into the cavity from the holder.

21. The apparatus of claim 19 wherein a proximal end portion of the needle projects inward in the cavity beyond the hub for puncturing a stopper on a vial inserted within the cavity.

22. The apparatus of claim 19 wherein the wall comprises a first portion having relatively large diameter extending from the second end to the inward extension and a second portion having a relatively small diameter extending from the inward extension to the first end.

23. The apparatus of claim 19 wherein the receiver comprises a generally cylindrical recess in the second end between the restricted opening and the cavity, and wherein the connector comprises means for cooperating with the generally cylindrical wall.

24. The apparatus of claim 19 wherein the cylindrical wall is threaded with female threads and wherein the connector is threaded with complementary male threads.

25. The apparatus of claim 24 wherein the threads are discontinuous for rapid disassembly upon relative parial turning.

26. A self-resheathing safety needle for syringes comprising a longitudinally extending case having a first relatively open end and a second relatively closed end and having a wall extending between the first and second ends thereby forming a cavity, an inward extension on the wall extending inward in the cavity near the first end for preventing passage of a needle assembly, the second end having a central nipple portion extending outward from the case for receiving a snap-off needlecovering cap, and the second end having a receiver for receiving and releasably holding a needle assembly, a needle assembly having an elongated needle having sharpened distal end and a hub mounted on the needle and tightly gripping the needle at a proximal end opposite the sharpened end, the hub having a connector for cooperating with the receiver to releasably hold the hub in the receiver with a distal end portion of the needle extending through a small opening in the nipple, the hub further having a flange for contacting the inward extension when the needle is released from the receiver and is withdrawn into the cavity and thereby and preventing outward egress of the needle assembly from the cavity through the first end of the case.

27. The apparatus of claim 26 wherein the hub comprises a tapered recess for receiving a nozzle portion of a syringe body and wherein the inward extension is configured for permitting passage of the syringe body into the casing.

28. The apparatus of claim 26 further comprising a syringe body having a nozzle portion tightly slidingly connected to the hub, the syringe body being mounted inside the cavity within the inward extension and a plunger compressed in the syringe body, and wherein the flange extends radially outward beyond the syringe body.

29. The apparatus of claim 26 wherein the receiver comprises a generally cylindrical recess in the second end between the restricted opening and the cavity, and wherein the connector comprises means for cooperating with the generally cylindrical wall.

30. The apparatus of claim 29 wherein the connector comprises an externally longitudinally ribbed structure, whereby ribs releasably engage the generally cylindrical wall of the receiver.

* * * * *